United States Patent [19]

Seng et al.

[11] 3,984,547

[45] Oct. 5, 1976

[54] VETERINARY FEEDSTUFFS

[75] Inventors: Florin Seng, Cologne-Buchheim; Kurt Ley, Odenthal-Globusch; Karl Georg Metzger, Wuppertal-Elberfeld, all of Germany

[73] Assignee: Bayer Aktiengesellschaft, Germany

[22] Filed: Mar. 28, 1975

[21] Appl. No.: 562,879

Related U.S. Application Data

[62] Division of Ser. No. 399,098, Sept. 20, 1974, which is a division of Ser. No. 323,953, Jan. 15, 1973, Pat. No. 3,856,957, which is a division of Ser. No. 130,007, March 31, 1971, Pat. No. 3,819,616.

[30] Foreign Application Priority Data

July 21, 1971 Germany............................ 2015676

[52] U.S. Cl.............................. 424/248; 424/250; 424/246
[51] Int. Cl.² ............... A61K 31/495; A61K 31/535

[58] Field of Search..................... 424/250, 248, 246

[56] References Cited
UNITED STATES PATENTS

| | | | |
|---|---|---|---|
| 3,371,090 | 2/1972 | Johnston......................... | 260/240 G |
| 3,660,398 | 5/1972 | Ley et al......................... | 260/250 R |

FOREIGN PATENTS OR APPLICATIONS

| | | | |
|---|---|---|---|
| 1,215,815 | 12/1970 | United Kingdom............. | 260/250 R |

*Primary Examiner*—Jerome D. Goldberg
*Assistant Examiner*—Allen J. Robinson

[57] ABSTRACT

Imines of 2-formylquinoxaline-3-carboxylic acid-1,4-dioxides and their salts are obtained through treatment of the lactone or a salt of 2-dihydroxymethylquinoxaline-N,N-dioxide-3-carboxylic acid with a reactant bearing a free primary amino group. Veterinary feedstuffs are produced by combining a nutritious material with an imine as above described.

22 Claims, No Drawings

VETERINARY FEEDSTUFFS

This is a divisional of our copending application Ser. No. 399,098 filed Sept. 20, 1974; which is a divisional of our application Ser. No. 323,953 filed Jan. 15, 1973, now U.S. Pat. No. 3,856,957 issued Dec. 24, 1974; which itself is a divisional of our application Ser. No. 130,007, filed Mar. 31, 1971, now U.S. Pat. No. 3,819,616 issued June 25, 1974.

The present invention relates to new imines of 2-formyl-quinoxaline-3-carboxylic acid-1,4-dioxides and their salts, to processes for their preparation, to the use of the new compounds as medicaments in human medicine and veterinary medicine, to their use as feedstuff additives, especially in raising young animals or fatstock, and to compositions adapted to this use.

The new imines and salts have the general formula:

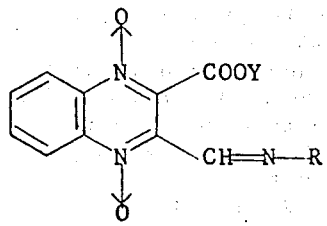

(1)

wherein
Y is hydrogen, an alkali metal cation or the cation $R^5$-$N^+H_3$; and each of R and $R^5$ is identical to or different from the other and is selected from the group consisting of
a. alkyl, substituted alkyl or cycloalkyl;
b.

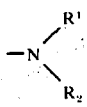

in which each of $R^1$ and $R^2$ when taken independently is identical to or different from the other, and is selected from the group consisting of hydrogen, alkyl or substituted alkyl, or when $R^1$ and $R^2$ are taken together with the nitrogen atom to which they are attached a 5- to 7-membered heterocyclic ring optionally containing as a ring member oxygen, sulphur, $SO_2$ or N-alkyl;
c.

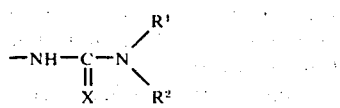

in which X is O, S or NH and, $R^1$ and $R^2$ are as above defined;
d.

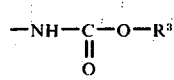

in which $R^3$ is alkyl or substituted alkyl;
e.

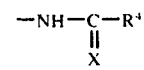

in which $R^4$ is phenyl, pyridyl or norbornyl, and X is as defined above;
f.

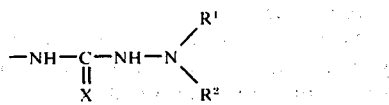

in which $R^1$, $R^2$ and X are as defined above; or
g.

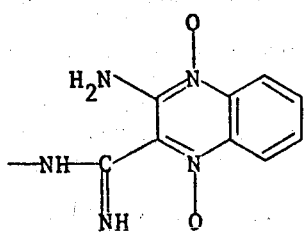

A preferred group of the imines and salts of the invention are those of the above general formula (1), in which:
Y has the meanings given above;
Each of R and $R^5$ is identical to or different from the other, and is selected from the group consisting of
a. alkyl or hydroxyalkyl of from 1 to 4 carbon atoms or a 6-membered or 7-membered monocyclo- or bicycloalkyl group;
b.

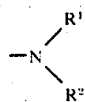

in which each of $R^1$ and $R^2$ when taken independently is identical to or different from the other and is selected from the group consisting of hydrogen, alkyl or hydroxyalkyl of from 1 to 4 carbon atoms, or when $R^1$ and $R^2$ are taken together with the nitrogen atom to which they are attached, a 6-membered heterocyclic ring optionally containing as a ring member oxygen or $SO_2$;
c.

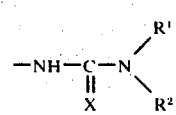

in which X is O, S or NH, and $R^1$ and $R^2$ are as herein defined;
d.

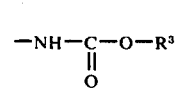

in which $R_3$ is alkyl or hydroxyalkyl of from 1 to 4 carbon atoms; and c.

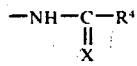

in which $R^4$ is phenyl, pyridyl or norbornyl, and X is as herein defined.

Alphatic groups embraced by R and $R^5$ include straight-chain or branched alkyl groups of from 1 to 6, preferably 1 to 4, carbon atoms. Cycloaliphatic radicals contain from 3 to 7, preferably 5 to 7, carbon atoms and include both monocyclic and bicyclic ring systems.

These aliphatic or cycloaliphatic groups can be optionally substituted, for example, by hydroxy, alkoxy, or acyloxy, the alkoxy and acyloxy groups containing 1 to 4, preferably 1 or 2, carbon atoms. The hydroxy group is the preferred substituent. Typical aliphatic and cycloaliphatic groups thus include methyl, ethyl, n-propyl, isopropyl, n-butyl, isobutyl, tert.-butyl, n-pentyl, isopentyl, hexyl, 2-hydroxyethyl, cyclopropyl, cyclopentyl, cyclohexyl, bicyclo-(2,2,1)-heptyl (norbornyl), and the like.

The substituents $R^1$ and $R^2$ are hydrogen or alkyl of from 1 to 4, preferably 1 or 2, carbon atoms. These alkyl groups can be optionally substituted with hydroxy, alkoxy or acyloxy, alkoxy and acyloxy groups containing 1 to 4, preferably 1 or 2, carbon atoms. Thus included are ethyl, n-propyl, isopropyl, n-butyl, isobutyl and tert.-butyl, as well as the corresponding groups substituted by hydroxy.

$R^1$ and $R^2$ when taken together with the nitrogen atom to which they are attached, can also form a heterocyclic ring, preferably containing 6 ring members, and preferably with an oxygen atom, a sulphur atom, an N-alkyl group containing 1 to 4, preferably 1 or 2, carbon atoms, or the $SO_2$ group, as a ring member in the p-position relative to the nitrogen atom to which $R^1$ and $R^2$ are attached.

$R^3$ is an alkyl of from 1 to 4, preferably 1 or 2, carbon atoms which may also be optionally substituted by hydroxy, alkoxy, acyloxy, alkoxy and acyloxy containing 1 to 4, preferably 1 or 2, carbon atoms. The hydroxy group is a particularly preferred substituent. $R^3$ thus embraces such groups as methyl, ethyl, 2-hydroxyethyl and the like.

The alkali metal cation Y is, for example, that of sodium or potassium, preferably that of sodium.

$R^4$ is phenyl, pyridyl or norborn-2-yl. When $R^4$ is pyridyl, it can be bonded in the 2-, 3- or 4-position relative to the pyridyl nitrogen atom.

The above class of imines are obtained according to the process of the present invention by treatment of 1-oxo-3-hydroxy-1,3-dihydro-furo-(3,4-b)-quinoxaline-4,9-dioxide, which has the formula:

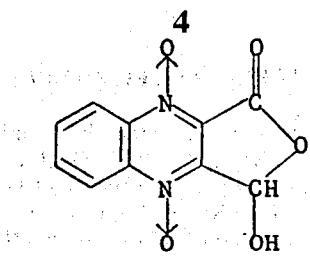

or a salt thereof of the formula

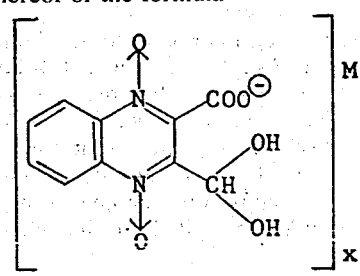

with an amine of the general formula $H_2N-R$, in which R is as previously defined, M is an alkali metal or alkaline earth metal cation and $x$ is 1 or 2.

The salts of the formula can be obtained from the lactone of formula through treatment with alkali metal or alkaline earth metal hydrogen carbonates.

M is preferably the cation of sodium, potassium or most preferably calcium.

Both inorganic and organic polar solvents can be used as diluents for the reaction according to the invention, such as for example water, lower aliphatic alcohols of 1 to 4 carbon atoms, lower aliphatic nitriles such as acetonitrile, tetrahydrofurane, dioxane, dimethoxyethane, pyridine, dimethylformamide and the like.

The reaction according to the invention is carried out at a temperature of about 0° C to about 50° C, preferably 20° C to about 35° C.

In practice, the lactone or lactone salts are dissolved or suspended in the diluent, and this solution or suspension is then treated with an appropriate quantity of the amine. The formation of the imine or of the imine salt takes place in a weakly exothermic reaction and the final product is then isolated through conventional methods.

The imine salts (1) can also be prepared by the reaction of the free acids with amines.

The salts may be obtained in a subsequent step by conventional techniques or directly in the reaction of the lactone with the amine. If about 2 mols of the amine per mole of lactone are employed, the product will be in the form of that amine salt. If an alkali metal salt or alkaline earth metal salt of the lactone is employed, or if it is desired to obtain the free acid from the lactone, only about 1 mol of the amine per mol of the lactone or salt is required.

The course of the process according to the invention can thus be illustrated by the following equations:

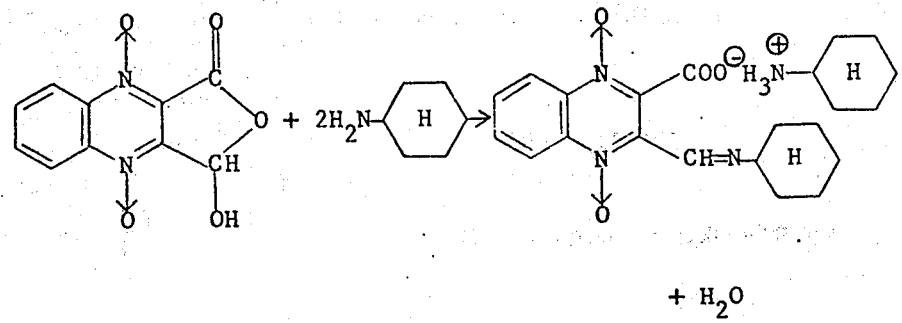

$+ H_2O$

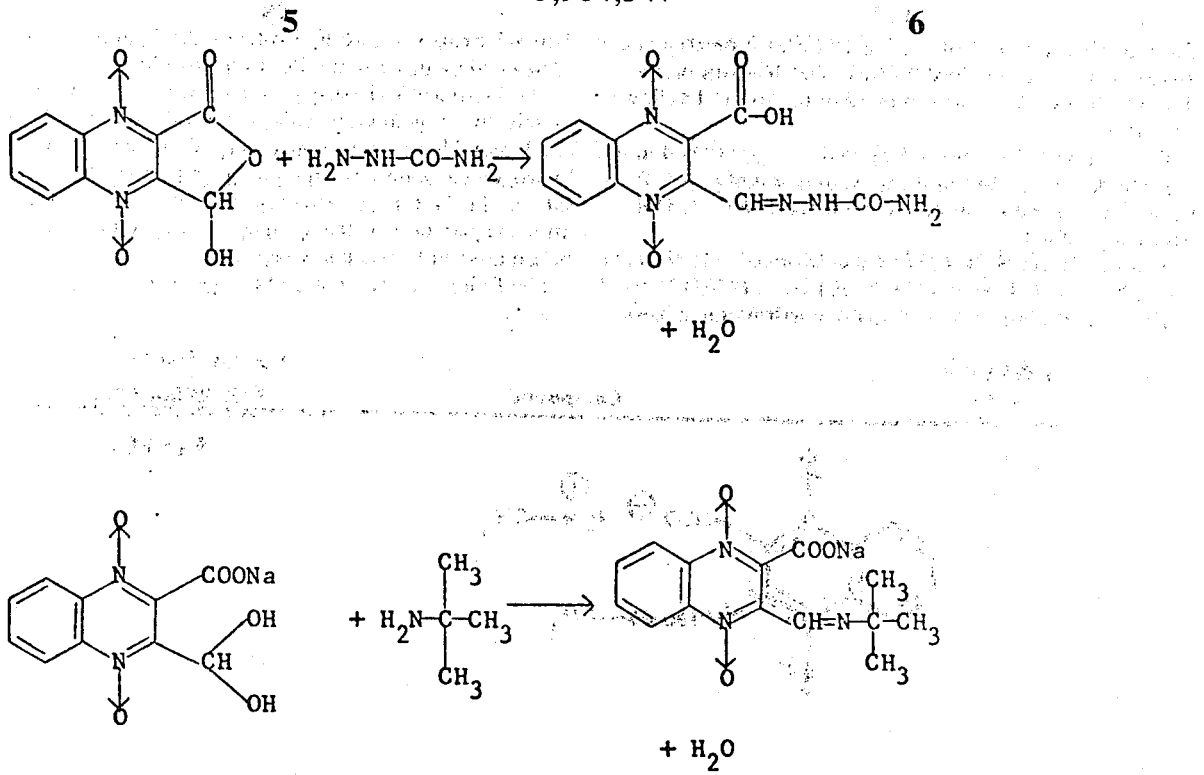

The following examples will serve to further typify the nature of this invention without being a limitation on the scope thereof.

EXAMPLE 1

23.4 g (0.1 mol) of 1-oxo-3-hydroxy-1,3-dihydrofuro-(3,4-b)-quinoxaline-4,9-dioxide are suspended in 60 ml of water and 20 G (0.2 mol) of 60% strength aqueous isopropylamine solution are added. The temperature is kept below 30° C by slight cooling. After a few minutes, a clear solution is produced. Evaporation in vacuo yields 45 g of the compound of the formula

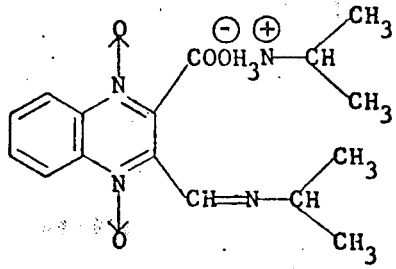

in the form of yellow crystals, which after recrystallisation from isopropanol melt at 123°–25° C, with decomposition.

Analysis: $C_{16}H_{22}N_4O_4$ (molecular weight 334) Calculated: C, 57.5%; H, 6.6%; N, 16.8%. Found: C, 57.1%; H, 5.8%; N, 16.8%.

EXAMPLE 2

27.4 g (0.1 mol) of the Na salt of 2-(di-hydroxymethyl)-3-carboxylic acid-quinoxaline-di-N-oxide are dissolved in 100 ml of water and 7.3 g (0.1 mol) of tert.-butylamine are added. The temperature is kept at 25° C by cooling. After 1 hour, the solution is evaporated in vacuo and 32 g of the compound of the formula

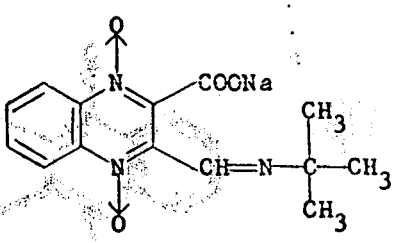

ae obtained in the form of yellow crystals which after recrystallisation from acetonitrile/water melt at 228° C, with decomposition.

Analysis: $C_{14}H_{14}N_3NaO_4$ (molecular weight 311) Calculated: C, 54.0%; H, 4.5%; N, 13.5%; Na, 7.4%. Found: C, 53.7%; H, 4.9%; N, 13.5%; Na, 6.9%.

The 1-oxo-3-hydroxy-1,3-dihydro-furo(3,4-b)-quinoxaline-4,9-dioxide of the formula (1) required as the starting compound can be obtained as follows:

30.7 g (0.1 mol) of 2-bismethoxy-methyl-3-dimethylaminocarbonyl-quinoxaline-1,4-di-N-oxide are introduced into 100 ml of 10% strength aqueous hydrochloric acid. A clear solution results, and after a short time the compound according to the invention separates out in the form of a yellow precipitate, which is filtered off after 6 hours. 17 g (72.6% of theory) of 1-oxo-3-hydroxy-1,3-dihydro-furo-(3,4-b)-quinoxaline-4,9-dioxide are thus obtained in the form of yellow crystals.

The compound is purified by dissolving it in sodium bicarbonate solution, filtering and acidifying the filtrate. The purified compound melts at 156° – 159°C, whilst foaming.

Analysis: $C_{10}H_6N_2O_5$ (235) Calculated: C, 51.3%; H, 2.6%; N, 12.0%. Found: C, 52.0%; H, 2.8%; N, 12.6%.

The alkali metal salts or alkaline earth metal salts of 1-oxo-3-hydroxy-1,3-dihydro-furo-(3,4-b)quinoxaline-4,9-dioxide can be manufactured as follows:

The lactone (9) is suspended in water and approximately the stoichiometrically required amount of the alkali metal hydrogen carbonate or alkaline earth metal hydrogen carbonate is added at room temperature. The salt of the lactone (10), thus produced, precipitates, after evaporation of the solution if necessary, and can be isolated in the usual manner.

The following are obtained analogously to Examples 1 and 2:

| Example No. | Compound | Melting Point (°C) (decomposition) |
|---|---|---|
| 3 | | 143–44 |
| 4 | | 85–86 |
| 5 | | 106 |
| 6 | | 138–40 |

-Continued
| Example No. | Compound | Melting Point (°C) (decomposition) |
|---|---|---|
| 7 | 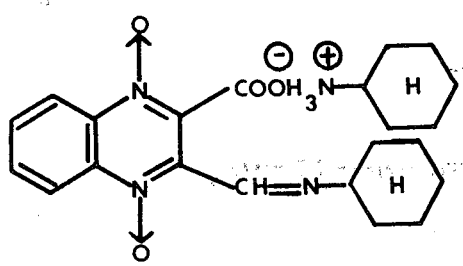 | 128-30 |
| 8 | 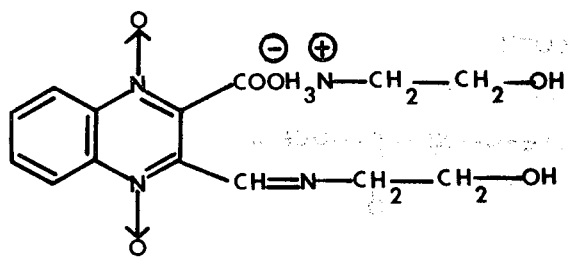 | 117-18 |
| 9 | 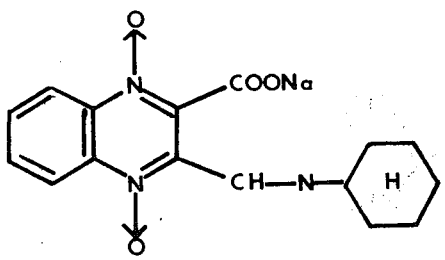 | 202 |
| 10 | 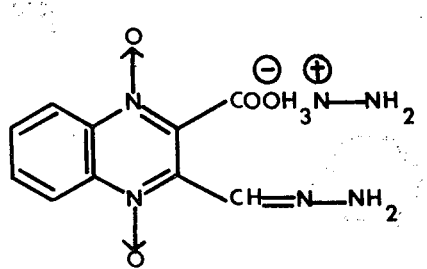 | 142 |
| 11 | 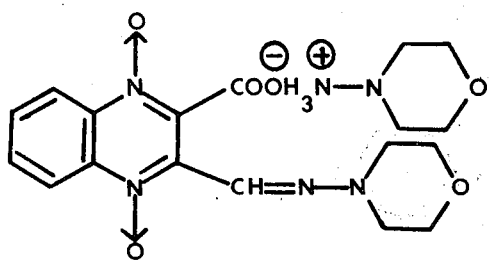 | 195-98 |

—Continued
| Example No. | Compound | Melting Point (°C) (decomposition) |
|---|---|---|
| 12 | 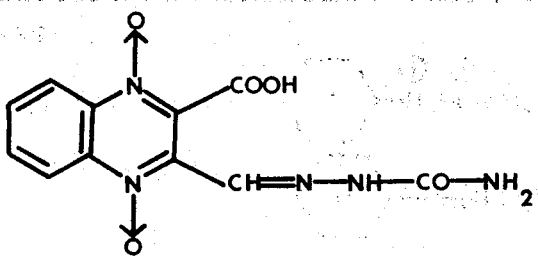 | 263 |
| 13 | 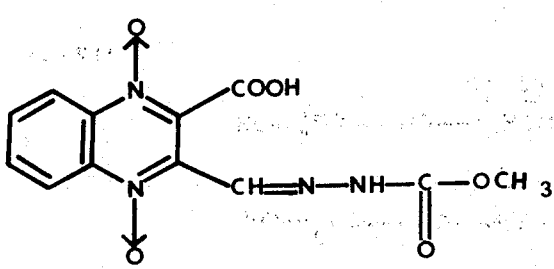 | 203–204 |
| 14 | 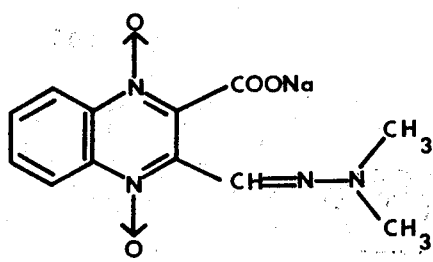 | 200 |
| 15 | 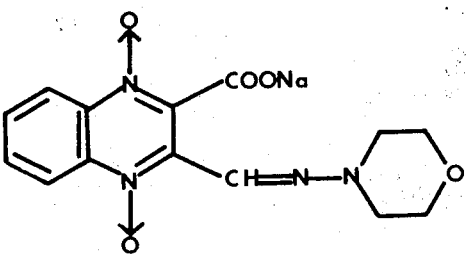 | 218 |
| 16 | 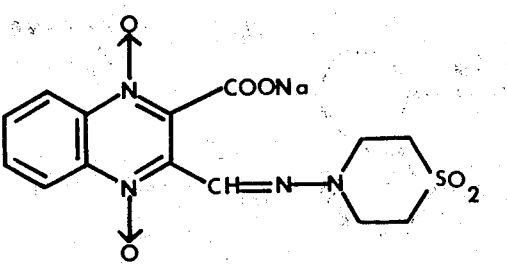 | 227 |

—Continued
| Example No. | Compound | Melting Point (°C) (decomposition) |
|---|---|---|
| 17 | 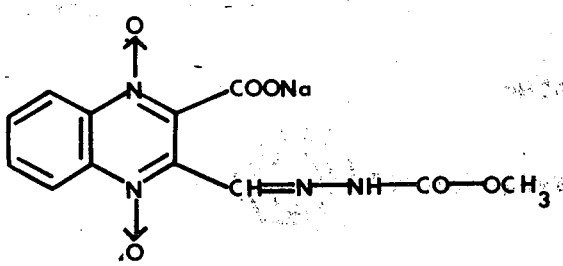 | 200 |
| 18 | 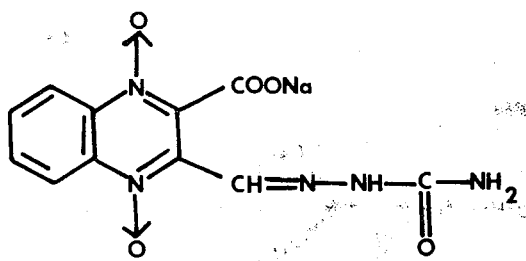 | 270 |
| 19 | 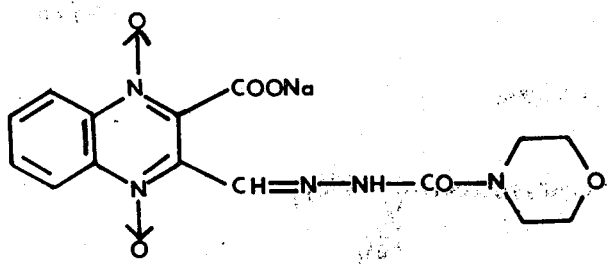 | 262 |
| 20 | 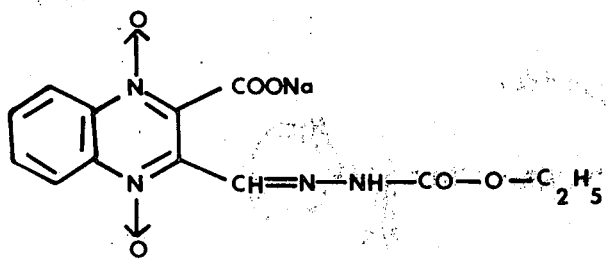 | 230 |
| 21 | 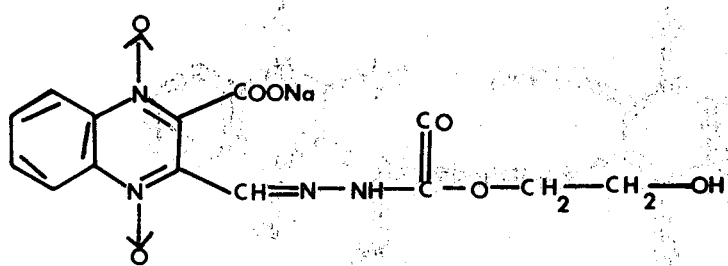 | 179 |

-Continued
| Example No. | Compound | Melting Point (°C) (decomposition) |
|---|---|---|
| 22 | 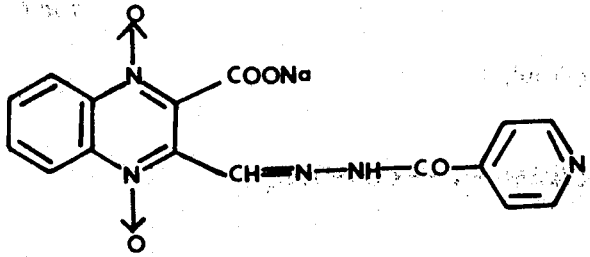 | 250 |
| 23 | 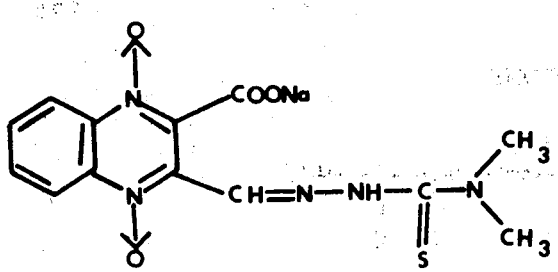 | 205 |
| 24 | 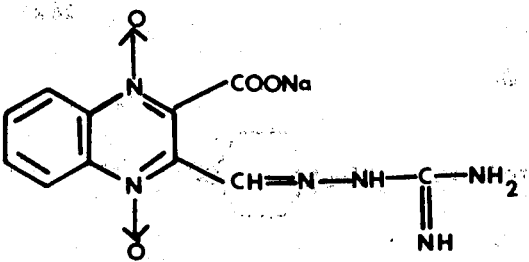 | 240 |
| 25 | 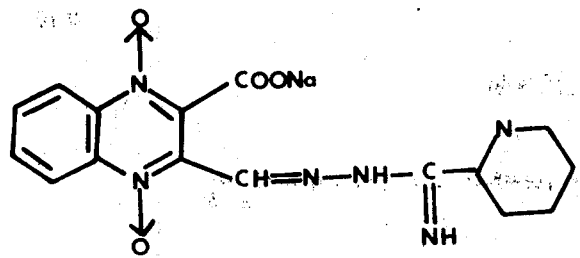 | 219 |
| 26 | 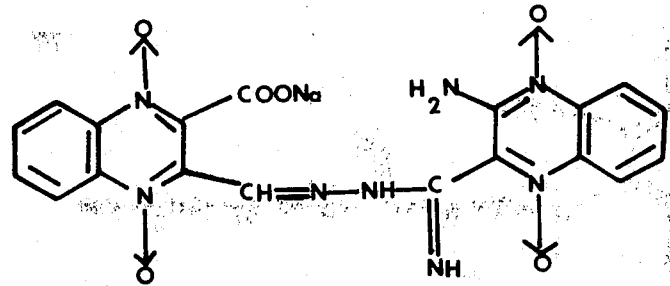 | 275 |

—Continued

| Example No. | Compound | Melting Point (°C) (decomposition) |
|---|---|---|
| 27 | 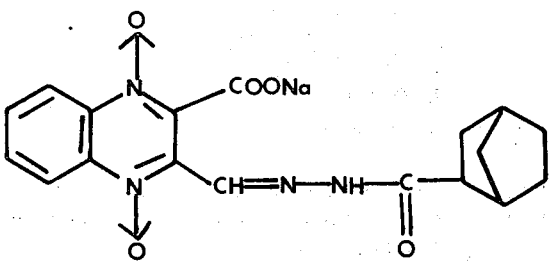 | 187 |
| 28 | 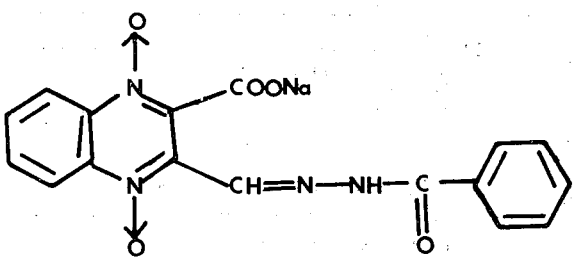 | 209 |
| 29 | 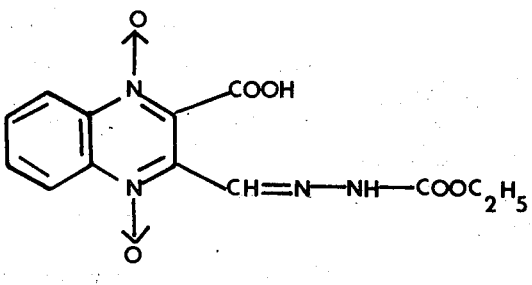 | 212-213 |
| 30 | 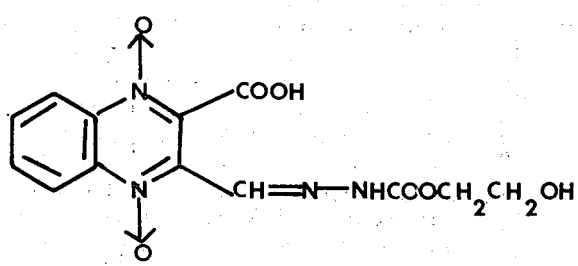 | 156-157 |

As has already been mentioned, the new compounds of the invention surprisingly show an excellent chemotherapeutic activity. Their chemotherapeutic action was examined both in animal experiments (oral and subcutaneous administration) with acute bacterial infections, and in vitro. In both cases the compounds show a very good antibacterial action, and the range of action encompasses both Gram-negative and Gram-positive bacteria. The chemotherapeutic activity of the compounds according to the invention permits their use in human medicine and in veterinary medicine. Furthermore, the compounds can be employed as feedstuff additives, especially in raising young animals or fatstock. The good in vitro and in vivo activity of the compounds according to the invention can be seen from Tables 1, 2 and 3 below.

The minimum inhibitory concentrations in vitro for some of the new compounds shown in Table 1 (MIC) were determined by the plate test in an agar medium of the following composition:

| proteose peptone | 10.0 g per liter |
| veal extract (solids) | 10.0 g per liter |

-continued

| | | |
|---|---|---|
| dextrose | 2.0 | g per liter |
| sodium chloride | 3.0 | g per liter |
| disodium phosphate | 2.0 | g per liter |
| sodium acetate | 1.0 | g per liter |
| adenine sulphate | 0.01 | g per liter |
| guanine hydrochloride | 0.01 | g per liter |
| uracil | 0.01 | g per liter |
| xanthin | 0.01 | g per liter |
| neutral agar | 12.0 | g per liter |

5.1 × 10³ germs were inoculated per plate.

5.10 × 10³ germs were inoculated per plate. Readings were taken after 24 and 48 hours, and the incubation temperature was about 37° C.

Table 1

| | MIC in γ/ml of medium | | |
|---|---|---|---|
| Bacterium | Compound of Example 10 | Compound of Example 12 | Compound of Example 13 |
| Escherichia coli A 261 | | | 20 |
| Escherichia coli C 165 | | | 50 |
| Proteus vulgaris species | | 150 | 10 |
| Pseudomonas aeruginosa Bonn | 100 | | 100 |
| Pseudomonas aeruginosa Walter | | | 100 |
| Klebsiella pneumonia 63 | | | 100 |
| Kletosiella pneumonia 8085 | | | 20 |
| Staphylococcus aureus 133 | | | 10 |
| Streptococcus pyogenes W | | | 100 |

Table 2

Minimum inhibitory concentration (MIC) in γ/ml of medium, measured by the series dilution test (complete medium), incubation temperatures: 37° C, determination of the MIC after 18, 24 and 48 hours.

| Bacterium | Compound of Example 13 |
|---|---|
| Streptococcus faecalis ATCC 9700 | 50 |
| Streptococcus faecalis ATCC 8564 | 100 |
| Streptococcus faecalis ATCC 8580 | 50 |
| Streptococcus faecalis ATCC 8698 | 100 |
| Streptococcus faecalis ATCC 8699 | 100 |
| Streptococcus faecalis ATCC 8711 | 50 |
| Streptococcus faecalis ATCC B. H. | 100 |
| Streptococcus faecalis ATCC Blaschke | 6-25 |
| Streptococcus faecalis ATCC 13 | 25 |
| Streptococcus faecalis ATCC species | 100 |
| Streptococcus faecalis ATCC liquef. | 50 |
| Streptococcus faecalis ATCC durans | 25 |
| Escherichia coli C 165 | 50-100 |
| Escherichia coli 2 | 25-50 |
| Escherichia coli 55 B 5 | 3-6 |
| Escherichia coli 14 | 12-25 |
| Escherichia coli A 261 | 25-50 |
| Escherichia coli 183/58 | 6-12 |
| Proteus mirabilis G | 12 |
| Proteus mirabilis 2935 | 12 |
| Proteus vulgaris 3400 | 50 |
| Proteus vulgaris 1017 | 17 |
| Pseudomonas aeruginosa W | 400 |
| Pseudomonas aeruginosa M | 25 |
| Pseudomonas aeruginosa B | 25 |
| Klebsiella ATCC 10031 | 1-2 |
| Klebsiella K 10 | 50 |
| Klebsiella 63 | 50 |
| Salmonella paratyphii BB II | 12 |
| Corynebacterium diphteriae gravis | 5-10 |
| Staphylococcus aureus 133 | 1 |
| Staphylococcus aureus 7705 | 12 |

-continued

| Bacterium | Compound of Example 13 |
|---|---|
| Staphylococcus aureus BRL | 12 |
| Neisseria catharalis N 1/41 | 6 |
| Mycoplasma gallisepticum | 6 |
| Mycoplasma gallisepticum*) | 6 |
| Mycoplasma granularum*) | 3 |
| Mycobacterium tuberculosis H 37 RV | 40 |

*)measured in a PPLO medium

For the compound of Example 3, the following minimal inhibitory concentrations (MIC) (γ/ml of nutrient medium) were measured by the series dilution test (PPLO medium), incubation temperature 37° C, determination after 18, 24 and 48 hours.

| Bacterium | MIC |
|---|---|
| Mycoplasma gallisepticum | 100 |
| Mycoplasma granularum | 25 |
| Mycoplasma bovirhinis | 200 |

In animal experiments on mice, the effective 100% dose ($ED_{100}$) in mg/Kg was determined for certain compounds of the invention after intraperitoneal infection and subcutaneous (s.c.) or oral (p.o.) administration of the preparation.

Table 3

| | Compound of Example 3 | | Compound of Example 8 | | Compound of Example 13 | | Compound of Example 14 | |
|---|---|---|---|---|---|---|---|---|
| Bacterium | s.c. | p.c. | s.c. | p.c. | s.c. | p.c. | s.c. | p.c. |
| Escherichia coli C 165 | 50 | 100 | 50 | 100 | 25 | 25 | 50 | 100 |
| Staphylococcus aureus 133 | — | — | — | — | 25 | 50 | — | — |

In general, it has proved advantageous, in acute general infections, to administer amounts of about 5 mg to about 200 mg per kilogram, preferably about 25 to about 50 mg per kilogram of body weight per day, to achieve effective results. Nevertheless it can at times be necessary to deviate from the amounts mentioned, in particular depending on the body weight of the test animal of patient or on the nature of the method of administration, but also because of the type of animal and its individual behaviour towards the medicament, or because of the nature of the formulation of the latter, and the point in time or interval at which administration takes place. Thus it can, in some cases, suffice to use less than the abovementioned minimum amount, whilst in other cases the upper limit mentioned must be exceeded. In the case of the administration of larger amounts it can be advisable to divide these into several individual doses over the course of the day. The same range of dosages is envisaged for administration in human medicine. The other comments made above also apply in a general sense.

Accordingly, the present invention provides a pharmaceutical composition containing as an active ingredient at least one of the new compounds of the general formula (1) given above in admixture with a pharmaceutically acceptable solid or liquid diluent or carrier as hereinafter defined.

In the present specification the expression "pharmaceutically acceptable diluent or carrier" means a non-toxic substance that when mixed with the active ingredient or ingredients renders it suitable for administration. The expression preferably excludes water and low-molecular weight organic solvents commonly used in chemical synthesis, except in the presence of other pharmaceutically necessary ingredients such as salts in correct quantities to render the composition isotonic, buffers, surfactants, colouring and flavouring agents, and preservatives. Examples of suitable liquid diluents and carriers are vegetable oils, glycerol, propylene glycol, polyols, buffered aqueous solutions, isotonic saline aqueous solutions, syrups and lotion bases. Examples of suitable solid diluents and carriers are starches, cellulose and its derivatives, sugars, stearates and stearic acid, talc, and ointment bases. Examples of pharmaceutical compositions according to the invention are ointments, pastes, creams, sprays, lotions, aqueous and non-aqueous suspensions, emulsions, and solutions (including parenterally injectable solutions), elixirs and syrups, and granulates and powders either free-flowing or compressed into tablets.

Pharmaceutical compositions of the invention adapted for oral administration are a preferred embodiment of the invention. The diluents and carriers used are preferably therefore those that adapt the active ingredient or ingredients for oral administration. Examples of such diluents and carriers are solid vehicles, excipients and lubricants such as glucose, lactose and sucrose, corn and potato starch, sodium carboxymethylcellulose, ethyl cellulose and cellulose acetate, powdered gum tragacanth, gelatin, alginic acid, agar, talc, stearic acid and sodium, calcium and magnesium stearates, sodium lauryl sulphate, polyvinyl-pyrrolidone, sodium citrate, calcium carbonate, and dicalcium phosphate.

The pharmaceutical compositions of the invention may also contain other non-toxic adjuvants and modifiers such as dyes, surfactants, perfumes, flavouring agents, such as sweeteners, preservatives and biocides.

Pharmaceutical compositions of the invention adapted for parenteral injection are another preferred embodiment of the invention. The diluents and carriers used are therefore preferably those that adapt the active ingredient for parenteral administration. Examples of diluents and carriers that adapt the active ingredient for parenteral administration are solvents and suspending diluents such as water, vegetable fatty oils, such as sesame oil, groundnut oil, corn oil, and cottonseed oil, aqueous propylene glycol, N,N'-dimethylformamide, and dimethyl sulphoxide. In general, any non-aqueous diluent can be used that does not reduce the activity of the active ingredient and is non-toxic in the dose employed.

For the administration of the water-soluble compounds of the invention by parenteral injection sterile aqueous solutions can be employed, and are within the scope of the pharmaceutical compositions of the invention. Such aqueous solutions should preferably when necessary be buffered in the usual manner, and the liquid diluent should preferably before administration be rendered isotonic by adding the requisite amount of salt or glucose. Such sterile buffered isotonic solutions are especially suitable for intravenous, intramuscular and intraperitoneal injections. These pharmaceutical compositions of the invention can further contain local anaesthetics or substances that promote the diffusion of the active ingredient, for example hyaluronidase.

The pharmaceutical compositions of the invention preferably contain 0.5 to 90 wt.% of at least one new compound of the invention.

The present invention also provides medicaments in dosage unit form as hereinafter defined comprising as an active ingredient at least one compound of general formula (1) given above either along or in admixture with a pharmaceutically acceptable solid or liquid diluent or carrier. In this case the diluent or carrier is preferably as defined above but can also be water or another common solvent.

The expression "medicament in dosage unit form" as used in the present specification means a medicament in the form of discrete portions each containing a unit dose or a multiple or sub-multiple of a unit dose of the active ingredients(s); for example, one, two, three or four unit doses or a half, a third or a quarter of a unit dose. A "unit dose" is the amount of the active ingredient(s) to be administered on one occasion and will usually be a daily dose, or for example a half, a third, or a quarter of a daily dose depending on whether the medicament is to be administered once or, for example, twice, three times, or four times a day.

The discrete portions constituting the medicament in dosage unit form can include a protective envelope. The active ingredient can be undiluted and contained in such an envelope, or can be mixed with a pharmaceutically acceptable solid or liquid diluent or carrier as defined above. Such portions can for example be in monolithic coherent form, such as tablets, lozenges, pastilles, pills, suppositories, or dragees; in wrapped or concealed form, the active ingredients being within a protective envelope, such as wrapped powders, cachets, sachets, capsules, or ampoules; or in the form of a sterile solution suitable for parenteral injection, such as ampoules of buffered, isotonic, sterile, pyrogen-free aqueous solution; or in any other form known in the art.

As stated above, peroral administration is a preferred mode of administration. Preferred medicaments in dosage unit form according to the invention are therefore those adapted for oral administration, such as tablets, pills, dragees, capsules, and cachets, as well as wrapped powders containing the active ingredients in powdered form with a powered diluent or carrier for suspension in water before being taken.

As also stated above a further preferred mode of administration is parenteral administration. Preferred medicaments in dosage unit form according to the invention are therfore those adapted for parenteral injection, such as ampoules containing a measured quantity of a sterile isotonic saline injectable aqueous solution of the new active ingredient, which may be buffered with a pharmaceutically acceptable buffer and are preferably free of pyrogens.

The preferred unit dose for administration of the medicaments of the invention is 250 – 16000 mg. of active ingredient, preferably 1250 – 4000 mg. This will usually be administered once daily.

The invention further provides a method of combatting bacterial infection in an animal which comprises administering to the animal (preferably parenterally or perorally) an effective amount of one of the new compounds, either alone, as a pharmaceutical composition according to the invention, or as a medicament in dosage unit form according to the invention.

Indications envisaged in human medicine are especially general infections, and infections of the efferent urinary tract, caused by Gram-positive and Gram-negative bacteria and by mycoplasma, and in veterinary medicine are general infections caused by Gram-negative and Gram-positive bacteria and my mycoplasma. Infections of the respiratory passages in poultry, especially in chicks, and mastitis of cows, may be mentioned particularly The new compounds can, as has already been mentioned, also be employed as a feedstuff additive, predominantly in raising young animals, especially chicks and fatstock.

The preparations can be administered in the feedstuff, special feedstuff preparations and feedstuff concentrates, but also via the drinking water.

The invention therefore also provides animal feedstuffs and feedstuff concentrates containing at least one of the new compounds of general formula (1).

The administration of the new compounds together with the feedstuff or feedstuff preparations and/or with the drinking water makes it possible to prevent or treat infections by both Gram-negative and Gram-positive bacteria and mycoplasma, and can furthermore contribute to better utilization of the feedstuff. As examples of frequently occurring veterinary illnesses which cause considerable economic damage and which can be prevented or treated by administering the new compounds in the feedstuff or in the drinking water, there may be mentioned, in addition to general infections, infection of the air sac in chicks, and mastitis in cows.

We claim:

1. A verterinary feedstuff which comprises a growth promoting amount of a compound of the formula

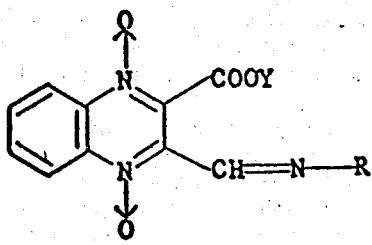

or a pharmaceutically acceptable non-toxic salt thereof wherein Y is hydrogen, an alkali metal cation or the cation $R^5-N^+H_3$; and each of R and $R^5$ is identical to or different from the other and is

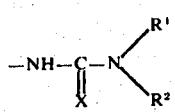

in which
X is O,S or NH and each of $R^1$ and $R^2$ when taken independently is identical to or different from the other, and is selected from the group consisting of hydrogen, alkyl of 1 to 4 carbon atoms and hydroxyalkyl of 1 to 4 carbon atoms or
when
$R^1$ and $R^2$ are taken together with the nitrogen atom to which they are attached, a 6-membered heterocyclic ring wherein the nitrogen atom is the only heteroatom or wherein oxygen or $SO_2$ is also present as a ring member in combination with a nutritious material.

2. The veterinary feedstuff according to claim 1 wherein when $R^1$ and $R^2$ are alkyl or hydroxyalkyl, the alkyl moieties contain 1 or 2 carbon atoms.

3. The veterinary feedstuff according to claim 1 wherein when $R^1$ and $R^2$ form a 6-membered heterocyclic ring with the nitrogen atom to which they are attached and said ring has oxygen or $SO_2$ present as a ring member, said oxygen or said $SO_2$ is in the p- position relative to the nitrogen atom to which $R^1$ and $R^2$ are attached.

4. The veterinary feedstuff according to claim 1 wherein Y is hydrogen.

5. The veterinary feedstuff according to claim 1 wherein Y is a sodium or potassium cation.

6. The veterinary feedstuff according to claim 1 in oral administration form.

7. The veterinary feedstuff according to claim 1 in subcutaneous administration form.

8. The veterinary feedstuff according to claim 1 wherein the compound is

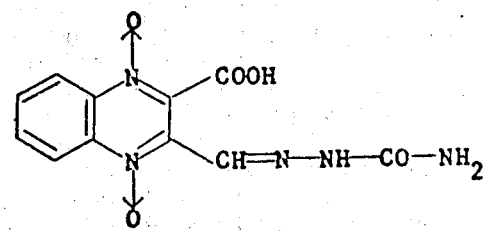

or a pharmaceutically acceptable non-toxic alkali metal or alkaline earth metal salt thereof.

9. The veterinary feedstuff according to claim 1 wherein the compound is

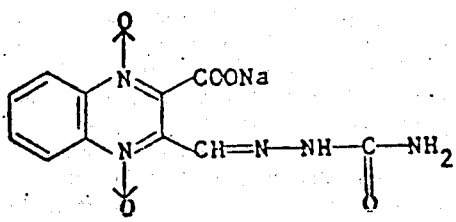

10. The veterinary feedstuff according to claim 1 wherein the compound is

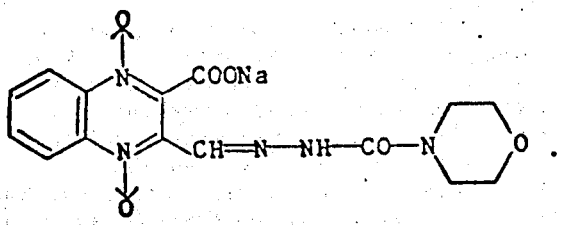

11. The veterinary feedstuff according to claim 1 wherein the compound is

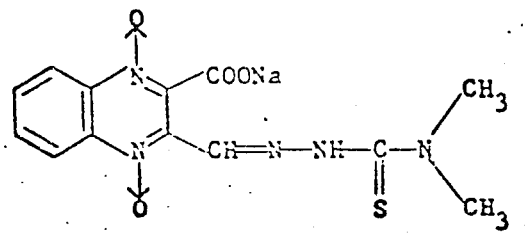

12. The veterinary feedstuff according to claim 1 wherein the compound is

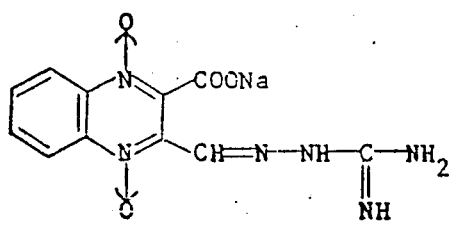

13. A method of promoting growth in animals which comprises feeding an animal a growth promoting amount of the feedstuff of claim 1.

14. The method according to claim 13 wherein $R^1$ and $R^2$ are alkyl or hydroxyalkyl, the alkyl moieties contain 1 or 2 carbon atoms.

15. The method according to claim 13 wherein when $R^1$ and $R^2$ form a 6-membered heterocyclic ring with the nitrogen atom to which they are attached and said ring has oxygen or $SO_2$ present as a ring member, said oxygen or said $SO_2$ is in the p-position relative to the nitrogen atom to which $R^1$ and $R^2$ are attached.

16. The method according to claim 13 wherein Y is hydrogen.

17. The method according to claim 13 wherein Y is a sodium or potassium cation.

18. The method according to claim 13 wherein the compound is

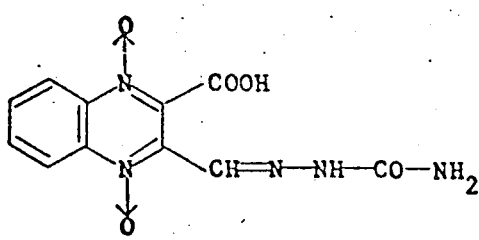

or a pharmaceutically acceptable non-toxic alkali metal or alkaline earth metal salt thereof.

19. The method according to claim 13 wherein the compound is

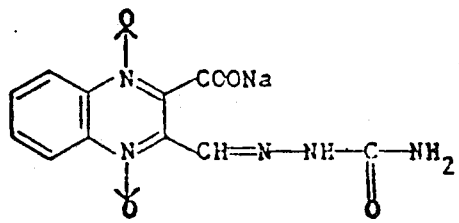

20. The method according to claim 13 wherein the compound is

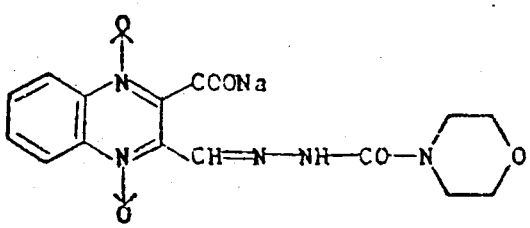

21. The method according to claim 13 wherein the compound is

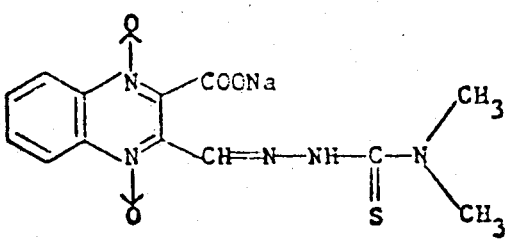

22. The method according to claim 13 wherein the compound is

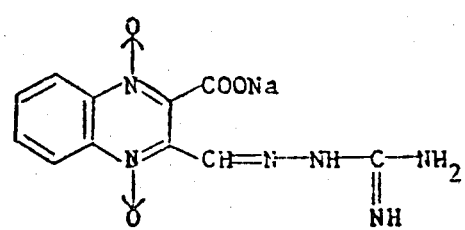

* * * * *

UNITED STATES PATENT AND TRADEMARK OFFICE
CERTIFICATE OF CORRECTION

PATENT NO. : 3,984,547
DATED : October 5, 1976
INVENTOR(S) : Florin Seng; Kurt Ley; and Karl Georg Metzger.

It is certified that error appears in the above—identified patent and that said Letters Patent are hereby corrected as shown below:

Filing date of German priority document 2015676 should be corrected to read -- April 2, 1970 --.

Signed and Sealed this

Fourteenth Day of December 1976

[SEAL]

Attest:

RUTH C. MASON
*Attesting Officer*

C. MARSHALL DANN
*Commissioner of Patents and Trademarks*